United States Patent [19]

Bradford et al.

[11] Patent Number: Plant 7,507

[45] Date of Patent: Apr. 23, 1991

[54] NECTARINE TREE (SPRING BRIGHT)

[76] Inventors: Norman G. Bradford, 11875 E. Savana Rd.; Lowell G. Bradford, 12439 E. Savana Rd., both of Le Grand, Calif. 95333

[21] Appl. No.: 457,236

[22] Filed: Dec. 26, 1988

[51] Int. Cl.[5] ..... A01H 5/00

[52] U.S. Cl. ..... Plt./41

[58] Field of Search ..... Plt./41

[56] References Cited

U.S. PATENT DOCUMENTS

P.P. 5,454 4/1985 Bradford ..... Plt. 41

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described in late June, with first picking on June 21, 1989, and is uniformly large in size, clingstone in type, fully dark red in skin color, slightly acidic but very sweet in flavor, and exceptionally firm in texture, resulting in excellent quality for keeping and shipping. The variety was developed as a hybridized seedling from the selected seed parent, May Diamond (U.S. Plant Pat. No. 5,454), and an unnamed seedling as the selected pollen parent.

1 Drawing Sheet

BACKGROUND OF THE NEW VARIETY

In a continuing effort to improve the quality of shipping fruits, we the inventors, typically hybridize a large number of nectarine, peach, plum, apricot, and cherry seedlings each year. The present invention relates to a new and distinct variety of nectarine tree, which was been denominated varietally as "Spring Bright". The present variety was hybridized by us in 1983, and the resulting seedling was planted in a cultivated area of our experimental orchard at Bradford Farms near Le Grand, Calif. in Merced County (San Joaquin Valley). Specifically, the hybridized seedling was originated by using May Diamond (U.S. Pat. No. 5,454) as the selected seed parent and an unnamed seedling as the selected pollen parent. Subsequent to origination of the present variety of nectarine tree, we asexually reproduced it by budding and grafting, and such reproduction of plant and fruit characteristics were true to the original plant in all respects.

The present variety ripens at nearly the same time period as Spring Red (U.S. Plant Pat. No. 3,619), but is distinguished therefrom and an improvement thereon by producing fruit that is darker in skin color, very much firmer in texture, much sweeter in flavor, and clingstone in type instead of freestone.

The present variety is similar to its selected seed parent, May Diamond (U.S. Plant Pat. No. 5,454), in fruit appearance by being a fully red colored nectarine with excellent firmness, but is distinguished therefrom by ripening sixteen days later, by being a clingstone instead of a freestone, by having a sweeter flavor. The tree is further distinguished from the May Diamond by producing a large instead of small blossom and by having globose instead of reniform glands.

DRAWING

The accompanying photograph exhibits three whole fruits positioned to display the characteristics of the skin color and form, one fruit halved around the suture to reveal the flesh, a stone that was cleaned and dried, a detached leaf, and branches with leaves attached, all typical of the subject variety.

POMOLOGICAL CHARACTERISTICS

Referring now more specifically to the pomological characteristics of this new and distinct variety of nectarine tree, the following has been observed under the ecological conditions prevailing at the experimental orchard of the inventors near Le Grand, Merced County (San Joaquin Valley), Calif. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed:
Hardiness: Hardy.
Production: Very productive.
Bearing: Regular bearer.
Trunk:
- *Size.*—Medium.
- *Texture.*—Medium.
- *Color.*—Grayish reddish brown [46. gy.rBr].
- *Lenticels.*—Numerous. Color: Light reddish brown [42. l.rBr]. Average size: 5/16" [7.9 mm.].

Branches:
- *Size.*—Medium.
- *Texture.*—Medium.
- *Color.*—1st year wood — Topside: Grayish red [19. gy.R] if exposed to sunlight. 1st year wood — Underside: Light yellow green [119. l.YG]. Older wood: Moderate brown [58. m.Br].
- *Lenticels.*—Numerous, very small.

Leaves:
- *Size.*—Large. Average length: 6" [152.4 cm.]. Average width: 1½" [38.1 mm.].
- *Thickness.*—Medium.
- *Form.*—Elliptical.
- *Apex.*—Acuminate.
- *Base.*—Acute.
- *Surface.*—Smooth.

*Color.*—Dorsal surface: Moderate olive green [125. m.OlG]. Ventral surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.].

*Glands.*—Numbers: Mostly 2 per leaf. Position: Some oppositely and some alternately positioned on petiole and base of blade. Size: Medium. Form: Globose. Color: Deep greenish yellow [100. deep gY].

*Stipules.*—Numerous. Average length: ¼" [6.4 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Medium, as compared with other varieties.

*Size.*—Large.

*Color.*—Varies from pinkish white [9. pkWhite] to moderate pink [5. m.Pk].

FRUIT

Maturity when described: Hard but eating ripe, June 24, 1989.

Date of first picking: June 21, 1989.

Date of last picking: June 29, 1989.

Size: Uniform, large.

*Average diameter axially.*—2¾" [69.9 mm.].

*Average traversely in suture plane.*—2½" [63.5 mm.].

Form: Uniform, slightly unsymmetrical, somewhat oblong.

*Longitudinal section form.*—Oval.

*Transverse section through diameter.*—Round.

Suture: A shallow depression extending from the base to slightly beyond the apex with a slight depression on both sides of the pistil point.

Ventral surface: Rounded, lipped toward the apex on both sides.

Lips: Slightly unequal.

Cavity: Flaring, circular, suture showing on one side.

Base: Rounded.

Apex: Rounded and slightly depressed.

Pistil point: Mostly oblique, very short, depressed within the suture.

Stem: Medium size.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed as of yet.

*Color.*—From very deep red [14. v.deep R] to strong red [12. s.R] over the entire surface with some light orange yellow [70.l.OY] freckling near the apex.

Flesh:

*Color.*—Vivid yellow [82. v.Y] to the pit except for a slight amount of deep pink [3. deep Pk] flecking very near the stone.

*Amygdalin.*—Moderate.

*Juice.*—Abundant, rich.

*Texture.*—Extremely firm, fine, crisp.

*Fibers.*—Abundant, fine, tender.

*Ripens.*—Evenly.

*Flavor.*—Slightly acidic and very sweet.

*Aroma.*—Pronounced.

*Eating quality.*—Very best.

STONE

Type: Clingstone.

Form: Elliptical.

Base: Straight.

Apex: Acute.

Sides: Equal.

Surface: Irregularly furrowed toward the apex and along the ventral edge, pitted toward the base.

Ridges: Slightly jagged.

Color: Light yellowish brown [76. l.yBr].

Pit wall: 3/16" [4.8 mm.] thick.

Tendency to split: None observed.

Kernel:

*Form.*—Oval.

*Taste.*—Sweet.

*Viable.*—Yes.

*Average width.*—7/16" [11.1 mm.].

*Average length.*—9/16" [14.3 mm.].

Skin color: Light yellow [86. l.Y] before drying.

Pellicle color: Light grayish brown [60. l.gy.Br].

Amygdalin: Scant.

USE

Market: Fresh market, both local and long distance shipping.

Keeping quality: Excellent.

Shipping quality: Excellent.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of clingstone nectarine tree, substantially as illustrated and described, whose fruit matures at nearly the same time as Spring Red (U.S. Plant Pat. No. 3,619), but is distinguished therefrom and an improvement thereon by producing fruit that is darker red in skin color, very much firmer in texture, much sweeter in flavor, and clingstone instead of freestone in type; whose fruit most nearly resembles the May Diamond (U.S. Plant Pat. No. 5,454), the seed parent, by being a full red colored nectarine with excellent firmness, but is distinguished therefrom and an improvement thereon by ripening sixteen days later, by being a clingstone instead of a freestone, and by having a sweeter flavor; and whose tree is distinguished from the May Diamond by producing a large instead of small blossom and by having globose instead of reniform glands.

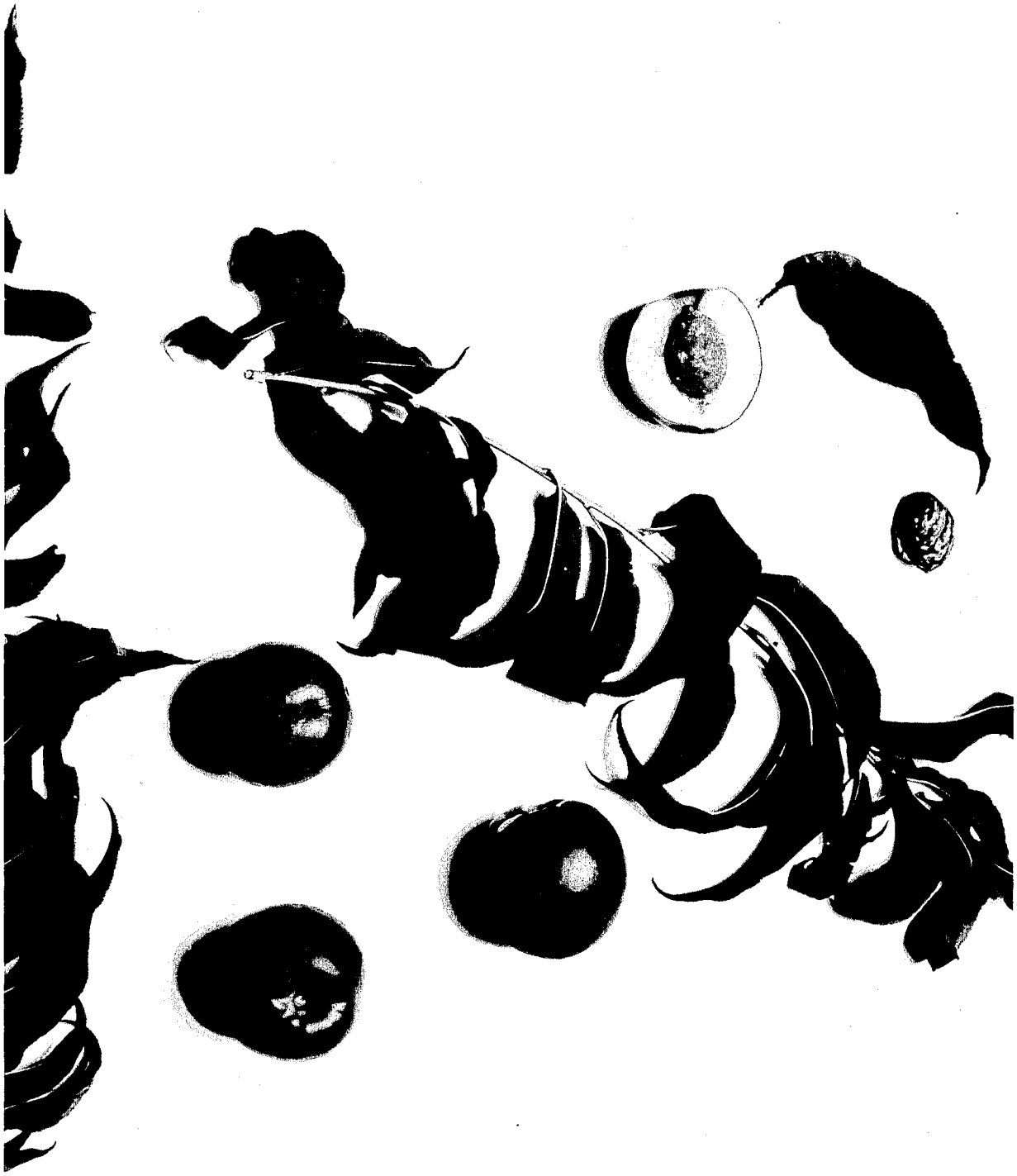

* * * * *